United States Patent [19]

Zinnen

[11] Patent Number: 5,225,580
[45] Date of Patent: Jul. 6, 1993

[54] PROCESS FOR SEPARATING FATTY ACIDS AND TRIGLYCERIDES

[75] Inventor: Hermann A. Zinnen, Evanston, Ill.

[73] Assignee: UOP, Des Plaines, Ill.

[21] Appl. No.: 568,576

[22] Filed: Aug. 16, 1990

[51] Int. Cl.$^5$ .............................................. C09F 7/00
[52] U.S. Cl. ..................... 554/30; 554/127; 554/191; 554/193
[58] Field of Search ............... 260/428, 428.5; 554/30, 554/127, 191, 193

[56] References Cited

U.S. PATENT DOCUMENTS

| | | | |
|---|---|---|---|
| 2,639,289 | 5/1953 | Vogel | 260/428 |
| 2,985,589 | 5/1961 | Broughton et al. | 210/34 |
| 3,040,777 | 6/1962 | Carson et al. | 137/625.15 |
| 3,328,439 | 6/1967 | Hamilton | 260/410.9 |
| 3,422,848 | 1/1969 | Liebman et al. | 137/625.15 |
| 3,706,812 | 12/1972 | De Rosset et al. | 260/674 SA |
| 4,048,205 | 9/1977 | Neuzil et al. | 260/428 |
| 4,061,724 | 12/1977 | Grose et al. | 423/335 |
| 4,275,081 | 6/1981 | Coleman et al. | 426/33 |
| 4,277,412 | 7/1981 | Logan | 260/428.5 |
| 4,284,580 | 8/1981 | Logan et al. | 260/428.5 |
| 4,353,838 | 10/1982 | Cleary et al. | 260/419 |
| 4,524,029 | 6/1985 | Cleary et al. | 260/419 |
| 4,642,397 | 2/1987 | Zinnen et al. | 568/934 |
| 4,770,819 | 9/1988 | Zinnen | 260/428.5 |

OTHER PUBLICATIONS

Wessels, Pure & Applied Chemistry, vol. 55, #8, pp. 1381-1385, 1983.

Primary Examiner—José G. Dees
Assistant Examiner—D. Carr
Attorney, Agent, or Firm—Thomas K. McBride; John F. Spears, Jr.; Jack H. Hall

[57] ABSTRACT

A two-stage separation process for separating highly unsaturated triglycerides from an interesterification reaction product by sequential chromatographic separations wherein triglycerides are separated from saturated fatty acids in the first stage and unsaturated fatty acids are recovered in the second stage for recycle to the interesterification reaction zone. In a preferred embodiment using silica gel and silicalite in the two stages, respectively, and heptanone as desorbent in both stages, triglyceride product is removed as the first stage raffinate and the unsaturated fatty acid recycle product stream is removed as the raffinate in the second stage. In another embodiment, using silicalite adsorbent in both stages and 2-heptanone and acetone in the first and second stages, respectively, saturated fatty acids are removed as the extract in the first stage and triglycerides and unsaturated fatty acids are separated as raffinate product and extract product for recycle, respectively.

16 Claims, 10 Drawing Sheets

PROCESS FOR SEPARATING FATTY ACIDS AND TRIGLYCERIDES

FIELD OF THE INVENTION

The field of art to which this invention belongs is the production of triglycerides having a high degree of unsaturation. More specifically, the invention relates to a process for reacting triglycerides with unsaturated fatty acids via a catalyzed interesterification reaction followed by a two-stage adsorptive separation process for separating free fatty acids from triglycerides.

BACKGROUND OF THE INVENTION

Interesterification reactions between triglycerides and free fatty acids have been used for upgrading triglyceride fats and oils, e.g., by increasing or decreasing the unsaturation of the fatty acid moieties in the triglyceride molecule. In U.S. Pat. No. 4,275,081, it is disclosed that the reaction may be catalyzed by positionally selective water-soluble microbial lipase enzymes. Prior art catalysts based on alkali metals or alkaline earth metals are also mentioned. It is disclosed that fatty acids liberated from the triglycerides participating in the reaction may be added to the free fatty acids contributing to the rearrangement of the fatty acid moieties on the triglycerides in the feed, but there is no disclosure of separating unreacted unsaturated fatty acids from the reaction effluent to return only the unsaturated free fatty acids to the reaction.

U.S. Pat. No. 3,328,439 discloses the use of chemical catalysts, e.g., natural and synthetic zeolitic aluminosilicates for the interesterification of glyceride oils.

The separation of many classes of compounds by selective adsorption on molecular sieves or zeolites as well as other adsorbents is well known. Also, various separations based on the degree of unsaturation are known, e.g., esters of saturated fatty acids from unsaturated fatty acids with X or Y zeolites exchanged with a selected cation from U.S. Pat. No. 4,048,205 to de Rosset and monoethanoid fatty acids from diethanoid fatty acids with cross-linked polystyrenes, e.g., "Amberlite" from U.S. Pat. No. 4,353,838 to Cleary et al. A process for separating a mixture of triglycerides, based on the iodine values, is shown in U.S. Pat. Nos. 4,277,412 and 4,284,580 in which permutite and aluminated silica gel adsorbents, respectively, can be used. The refining of oils by admixing them with magnesium silicate to adsorb coloring matter and free fatty acids from glyceride oils is disclosed in U.S. Pat. No. 2,639,289.

The use of silica gel in analytical chromatographic separations with various solvent systems is known. Particle sizes of silica gels used in analytical separations ranges from 3 to 10 microns. Also, the removal of various impurities from mixtures including triglycerides is known. Silica gel has been disclosed as an adsorbent for a bulk separation of fatty acids from triglycerides.

U.S. Pat. No. 4,524,029 to Cleary et al discloses a process for separating saturated fatty acids by selective adsorption of the saturated fatty acids onto a silicalite molecular sieve and desorbing the saturated fatty acids with a displacement fluid having a polarity index of at least 3.5. Silicalite is disclosed in Grose et al. U.S. Pat. No. 4,061,724.

U.S. Pat. No. 4,770,819 to Zinnen discloses the separation of diglycerides from triglycerides using an omega zeolite or silica as adsorbent and a ketone having up to 7 carbon atoms mixed with an n-aliphatic hydrocarbon mixture as the desorbent.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The functions and properties of adsorbents and desorbents in the chromatographic separation of liquid components are well known, but for reference thereto, Zinnen et al U.S. Pat. No. 4,642,397 is incorporated herein.

SUMMARY OF THE INVENTION

A major object of the invention is to provide a method for producing a highly unsaturated triglyceride oil, low in saturated fatty acid moieties, useful in certain food applications, from a feedstock comprising less unsaturated triglycerides and saturated triglycerides, combining an interesterification reaction step in which the feedstock triglycerides are reacted with unsaturated fatty acids or esters and sequential separation and purification steps in which the reaction product is separated into highly concentrated product streams, i.e., highly unsaturated triglycerides, unreacted unsaturated fatty acids and saturated fatty acids, by a two-stage adsorption separation process.

A feature of the invention is the removal of unsaturated fatty acids from the product streams by an adsorption separation process to provide a highly pure unsaturated triglyceride product and a suitable reactant for recycle to the interesterification reaction zone.

Another feature is the provision of an adsorptive separation process for separating free fatty acids from triglycerides with silicalite using a ketone desorbent having from 3 to 8 carbon atoms.

A third feature is the provision of an adsorptive separation process for separating saturated fatty acids from unsaturated fatty acids with silicalite and a preferred ketone desorbent having a low polarity index selected from the group, 2-heptanone and 3-heptanone.

Accordingly, a broad embodiment of the invention is directed toward a two-stage process for recovering polyunsaturated triglycerides from an interesterification reaction comprising treating a mixture of a triglyceride oil or fat and an unsaturated fatty acid or mixture of unsaturated fatty acids in an interesterification zone with a microbial lipase enzyme or chemical interesterification catalyst to increase the degree of unsaturation of said triglyceride oil or fat, contacting said treated triglyceride oil or fat in a first stage with an adsorbent more selective for saturated fatty acids than for triglycerides, removing a first raffinate product stream comprising polyunsaturated triglycerides produced in said interesterification reaction from said adsorbent, desorbing the saturated fatty acids produced in the interesterification reaction with a desorbent comprising a ketone, having from 3 to 8 carbon atoms, an ether or an ester, at desorption conditions, to produce a first extract product stream, contacting the product stream from said first stage containing unreacted unsaturated fatty acids with a second adsorbent in a second stage, capable of separating said unsaturated fatty acids from said first stage product stream, recovering said unsaturated fatty acids from said second adsorbent and recycling said unsaturated fatty acids to said interesterification zone and recovering a raffinate product comprising polyunsaturated triglycerides.

One specific embodiment of the invention is a two-stage process for recovering polyunsaturated triglycerides from an interesterification reaction comprising treating a mixture of a triglyceride oil or fat and unsaturated fatty acids in an interesterification zone with a microbial lipase enzyme or chemical interesterification catalyst to increase the degree of unsaturation of said triglyceride oil or fat, contacting said treated triglyceride with an adsorbent selective for saturated fatty acids, removing a raffinate comprising unreacted unsaturated fatty acids and the polyunsaturated triglycerides produced in said interesterification reaction from said adsorbent, desorbing the saturated fatty acids produced in said interesterification reaction with a desorbent comprising a ketone having from 3 to 8 carbon atoms, at desorption conditions, to produce an extract product stream, contacting said raffinate with a second adsorbent more selective for said unsaturated fatty acids, removing a second raffinate material comprising said polyunsaturated triglycerides, desorbing said unsaturated fatty acids with a desorbent comprising a ketone having from 3 to 8 carbon atoms, at desorption conditions and recycling said unsaturated fatty acids to said interesterification reaction.

Another specific embodiment of the invention is a two-stage process for recovering polyunsaturated triglycerides from an interesterification reaction comprising treating a mixture of a triglyceride oil or fat and an unsaturated fatty acid in an interesterification zone with a microbial lipase enzyme or chemical interesterification catalyst to increase the degree of unsaturation of said triglyceride oil or fat, contacting said treated triglyceride oil or fat in a first stage with an adsorbent selective for fatty acids, removing a raffinate material comprising polyunsaturated triglycerides produced in said interesterification reaction from said adsorbent, desorbing the saturated fatty acids produced in said interesterification reaction and unreacted unsaturated fatty acids with a desorbent comprising a ketone having from 3 to 8 carbon atoms, an ester or an ether, at desorption conditions, to produce a first extract product, contacting said first extract product from said first stage with a second adsorbent more selective for saturated fatty acids than unsaturated fatty acids, removing a second raffinate material comprising unsaturated fatty acids, desorbing saturated fatty acids with a desorbent comprising a ketone having from 3 to 8 carbon atoms, at desorption conditions and recycling said unsaturated fatty acids to said interesterification reaction.

Another specific embodiment of the invention is a process for separating unsaturated fatty acids from a mixture of fatty acids comprising saturated fatty acids and unsaturated fatty acids, comprising contacting said mixture of fatty acids with an adsorbent comprising silicalite, removing said unsaturated fatty acids from said adsorbent and desorbing said saturated fatty acids with a desorbent comprising a ketone selected from the group consisting of 2-heptanone and 3-heptanone, at desorption conditions.

Another specific embodiment of the invention is a process for separating fatty acids from a mixture of fatty acids and triglycerides, comprising contacting said mixture with an adsorbent comprising silicate, removing said triglycerides from said adsorbent and desorbing said fatty acids with a desorbent comprising ketones having from 3 to 8 carbon atoms, at desorption conditions. The most preferred ketones are those which are listed as acceptable for use in food products, e.g., 2-heptanone; 3-heptanone.

The desorbent materials useful for the preferred isothermal, isobaric, liquid-phase operation of the various stages of the process of my invention comprise low molecular weight ketones having from 3-8 carbon atoms. The ketones include acetone, methyl ethyl ketone, diethyl ketone, methylbutyl ketone, 2-heptanone, 3-heptanone, dipropyl ketone, 2-octanone, 3-octanone, etc. Also suitable are esters, including methyl butyrate, ethyl butyrate, methyl amylate, ethyl amylate, etc. and ethers, such as ethyl ether, methyl-t-butyl ether, phenyl ether, 3-methoxy hexane, anisole, glyme, diglyme, etc.

Other embodiments of my invention encompass details about feed mixtures, adsorbents, desorbent materials and operating conditions, all of which are hereinafter disclosed in the following discussion of each of the facets of the present invention.

DETAILED DESCRIPTION OF THE INVENTION

Terms used herein relating to the adsorptive separation process, such as "extract component" (extract), "raffinate component" (raffinate), extract or raffinate stream, extract or raffinate product, "desorbing material" (desorbent), "non-selective void volume" are used in their conventional meaning, for example, as defined in allowed U.S. Patent application Ser. No. 156,857 filed Feb. 17, 1988 in the name of Ou.

Highly unsaturated triglycerides are desirable oils for use in certain foods such a mayonnaise, salad dressings, cooking oil, etc. Such oils are also low in saturated fatty acid groups and in view of health concerns regarding the role of saturated fats in assessing risk of heart disease, some food products are being formulated with lower levels of saturated fats, e.g., less than about 1% saturated fatty acids, 2-4% diglycerides and 0.5% monoglycerides. Such triglycerides can be produced in several ways, but an important route is via an interesterification process wherein triglyceride oils with a low degree of unsaturation can be upgraded by reaction with unsaturated fatty acids. The process may be catalyzed enzymatically by a positionally selective lipose catalyst, e.g., *Candida cylindracal, Aspergillis niger, Geo-*

*trichum candidum* or various species of *Rhizopus* or chemically with an alkali metal or alkaline earth metal or zeolite catalyst. Such processes are disclosed, for example, in U.S. Pat. No. 4,275,081 (Unilever).

The triglyceride fats or oils which may be fed to the interesterification reaction include linseed oil, soybean oil, cotton seed oil, corn oil, peanut oil, palm oil, sunflower oil, safflower oil, tallow, lard, olive oil, canola oil or other naturally occuring or synthetic fats or oils.

Naturally occurring fats and oils containing substantial quantities of free fatty acids, especially unsaturated fatty acids, as well as triglycerides, may be fed directly to the separation process of the invention, e.g., palm oil, rice bran oil, etc. Partially refined oils or fats such as canola oil, soybean, safflower, cottonseed, sunflower or corn oil may also be used herein as the feedstock to the separation process.

Figure 1:
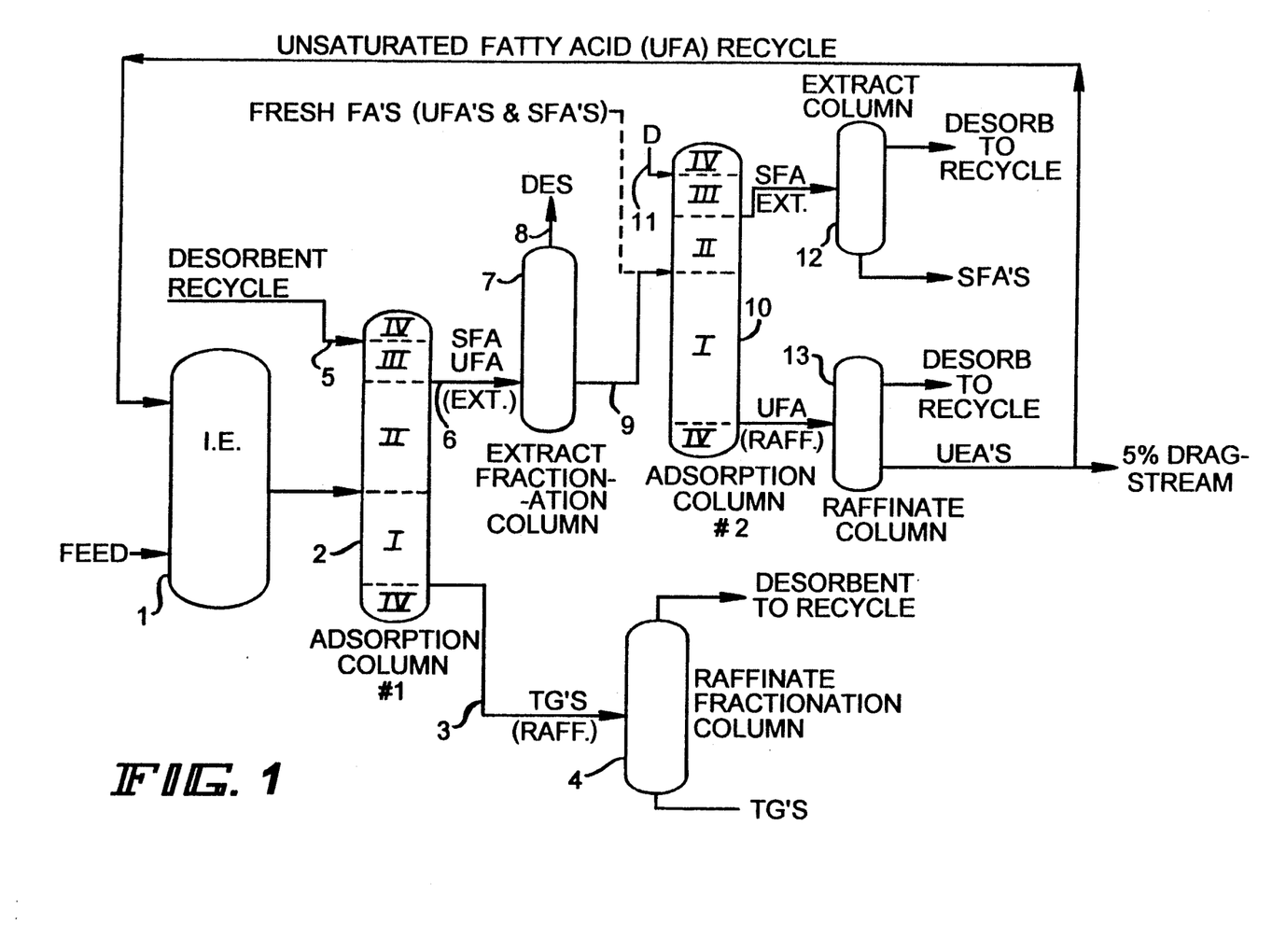
FIG. 1 is a flow scheme of the integrated process for making highly unsaturated triglycerides combining interesterification, a two-stage separation process and the recycle of recovered unsaturated fatty acids to the interesterification reaction zone.

The preferred scheme for producing unsaturated triglycerides (sometimes TG's) is shown in FIG. 1. The triglyceribed feed material is an oil, such as described above and is introduced into the interesterification reaction column 1 with unsaturated fatty acids (UFA's) recycled from the second stage of the separation process. In the interesterification reaction, the unsaturated fatty acid moieties replace the more saturated fatty acid groups of the triglyceride esters in the feed. The reaction may be catalyzed in several ways, two of the most widely utilized being a chemical catalyst such as natural and synthetic zeolitic aluminosilicates, e.g., as discussed in U.S. Pat. No. 3,328,439 and lipase enzymes, such as those disclosed in U.S. Pat. No. 4,275,081, supra. The effluent of the interesterification reaction column 1 is a mixture of triglyceride esters that are more highly unsaturated than the feed, saturated fatty acids produced in the reaction and unreacted unsaturated fatty acids. This effluent is fed into the first adsorption separation column 2, which preferably is operated as a countercurrent simulated moving bed system described in the aforementioned Broughton U.S. Pat. No. 2,985,589, where the triglycerides are separated as a class in the raffinate stream 3. Desorbent is removed in raffinate fractionation column 4 and purified highly unsaturated triglycerides are recovered as product.

The first stage adsorbent may be any adsorbent capable of making the class separation, i.e., preferentially adsorbing all the saturated and unsaturated fatty acids from the feed. The preferred adsorbent is silica gel, an amorphous silica having pore diameters of 7 or more Angstroms, a surface area ranging from 200 to 700 $m^2/g$, preferably 500 $m^2/g$, particle sizes from 16 to 80 mesh (U.S.), pore volume of 0.1 or more cc/g. Also useful are silicalite, dealuminated Y zeolite, $AlPO_4$-11 and $AlPO_4$-54. If silicalite is used in this stage, it is preferred that linolenic acid (C18:3) concentration be low because the 2-heptanone desorbent will cause the linolenic acid to be less strongly adsorbed and thereby contaminate the second stage raffinate triglyceride product. However, if this occurs, any C18:3 contamination can be remedied by refining, bleaching, deodorization or caustic extraction.

Silica gels illustrative of the range of values set forth above include: Davisil 646 silica gel, Davisil 636 silica gel and Bead Gel, all available from Davison Division of W. R. Grace & Co., and Merck 10181 silica gel. The values are set forth in the following table. Particle size of all the listed materials is in the range of 35-60 Mesh (U.S.).

TABLE 1

| Silica Gel | Pore Size (Å) | Pore Vol. (cc/g) | Surface Area (BET) (m²/g) |
|---|---|---|---|
| Davisil 646 | 150 | 1.15 | 300 |
| Davisil 656 | 60 | 0.75 | 480 |
| Merck 10181 | 40 | 0.68 | 675 |
| Bead-Gel | 22 | 0.45 | 800 |

Davisil 636 is preferred in the separation because of its greater capacity. The adsorbents used in the invention are also inert and have no exchangeable ions. The pore sizes are also large enough to enable adsorption of diglycerides, in order to eliminate some or all of the diglycerides from the non-adsorbed triglyceride raffinate product; in this regard, pore diameters of zeolites are too small to be useful.

The water content of the adsorbent affects the separation by reducing adsorptive capacity. The water content of the adsorbent, based on loss on ignition (LOI), is from 0 to 10% (wt.), preferably 0 to 5% (wt.). To reduce water content to the desired level, the adsorbent may be dried, e.g., at 80° C. in vacuum or 175° C. at atmospheric conditions or in nitrogen gas. Other sources of adsorbent deactivation may be the monoglycerides present in the feed or impurity amounts of glycerol, but these may be removed by washing the adsorbent with 2-heptanone.

The adsorbed fatty acids (saturated and unsaturated) are desorbed by a desorbent material, preferably a ketone having 3 to 8 carbon atoms, an ester or an ether. The ketones include acetone, methylethyl ketone, diethyl ketone, etc., and most preferably, 2- or 3-heptanone introduced into the adsorption column in desorbent input stream 5. Also suitable are esters such as ethyl butyrate and methyl-t-butyl ether, and ethers, such as glyme, diglyme, ethyl ether and phenyl ether.

The first stage extract stream 6 contains the preferentially adsorbed fatty acids, both the saturated and unsaturated fatty acids, and desorbent. The desorbent is recovered in an extract fractionation column 7 which is operated at fractionation conditions to produce an overhead fraction 8 which is recycled to the desorbent input stream. The bottoms stream 9, containing the unsaturated and saturated fatty acids is fed into a second adsorption column 10 to separate the unsaturated fatty acids from the saturated fatty acids. The second adsorbent column is operated in the same manner as the first, namely, a countercurrent simulated moving bed system. Desorbent is introduced into the second adsorption column 10 via line 11. In this second stage separation, the saturated fatty acids (SFA's) are preferentially adsorbed on the second stage adsorbent and are recovered in the extract stream 12 by desorbing the adsorbent with a desorbent. The extract stream containing saturated fatty acids and desorbent is fractionated in extract fractionation column 17. The unsaturated fatty acids are relatively non-adsorbed and are eluted first from the adsorbent as raffinate. Desorbent is removed from the raffinate stream 13 in a fractionation column 14 via the overhead 15. Desorbent recovered from fractionation columns 14 and 17 are recycled to one of the desorbent input streams 5 or 11. The unsaturated fatty acids are recovered as bottoms and recycled via line 16 to the interesterification column 1.

Fresh fatty acid makeup is also fed into the second adsorption column 10 via inlet 18 so that saturated fatty acids and $C_{20}$ and $C_{22}$ or higher unsaturated fatty acids can be removed from the fresh fatty acid makeup stream prior to the introduction of the unsaturated fatty acids into the interesterification column 1. A preferred source of unsaturated fatty acids is a hydrolyzed oil containing a high percentage of unsaturated fatty acids, for example, hydrolyzed canola oil, which contains about 94% (wt.) unsaturated fatty acids. A typical composition is shown in the following Table 2.

TABLE 2

| Hydrolyzed Canola Oil | |
|---|---|
| Fatty Acid Component | % |
| C14:0 | 0.1 |
| C14:1 | Trace |
| C16:0 | 3.6 |
| C16:1 | 0.2 |
| C18:0 | 2 |
| C18:1 | 57.1 |
| C18:1 (trans) | 2.9 |
| C18:2 | 19.8 |
| C18:2 | 0.2 |
| C18:3 | 1.2 |
| C18:3 | 6.7 |
| C18:3 | 1.2 |
| C20:0 | 0.5 |
| C20:1 | 1.5 |
| C22:0 | 0.2 |
| C22:1 | 0.4 |
| UNKNOWNS | 2.4 |
| TOTAL | 100 |

The major unsaturated components are oleic acid (C18:1) (57%) and linoleic acid (C18:2) (20%). Hydrolyzed canola contains less than 7% saturated fatty acids (mainly palmitic (C16:0) and stearic (C18:0)). It is important from an economic standpoint to recover the unreacted unsaturated fatty acids so that they can be recycled to the interesterification reaction and thus utilized in conversion of further triglyceride feed to more highly unsaturated triglycerides.

The second stage adsorbent is preferably silicalite, which preferentially adsorbs saturated fatty acids from a mixture with unsaturated fatty acids. Although other ketones having from 3 to 8 carbon atoms may also be used, the preferred second stage desorbents are heptanones, i.e., 2-heptanone and 3-heptanone or mixtures thereof because they are considered safe for the production of food materials and are stronger than prior art desorbents such as methyl ethyl ketone and acetone. The greater strength of the heptanones as desorbents for this separation result in lowering the fatty acid net retention volume, thus lowering the volume of desorbent required in the system. It may also enhance the extraction by the adsorbent, silicalite, of the higher molecular weight unsaturated acids, such as $C_{20}$ and $C_{22}$, which are less desirable fatty acid groups in the triglyceride product. An added economic benefit exists when the same desorbent can be used in both stages. Since heptanones, e.g., 2-heptanone or 3-heptanone, are excellent desorbents for both seprations, in the most preferred embodiment, 2-heptanone or 3-heptanone or a mixture of them are the preferred desorbents. However, this result was most unexpected in view of the disclosure in Cleary et al U.S. Pat. No. 4,524,029 supra limiting ketone desorbents in the separation of unsaturated fatty acids for saturated fatty acids to those having a polarity index (P.I.) greater than about 3.5. The P.I. of 2-heptanone and 3-heptanone are estimated to be about 2.5.

Figure 2:
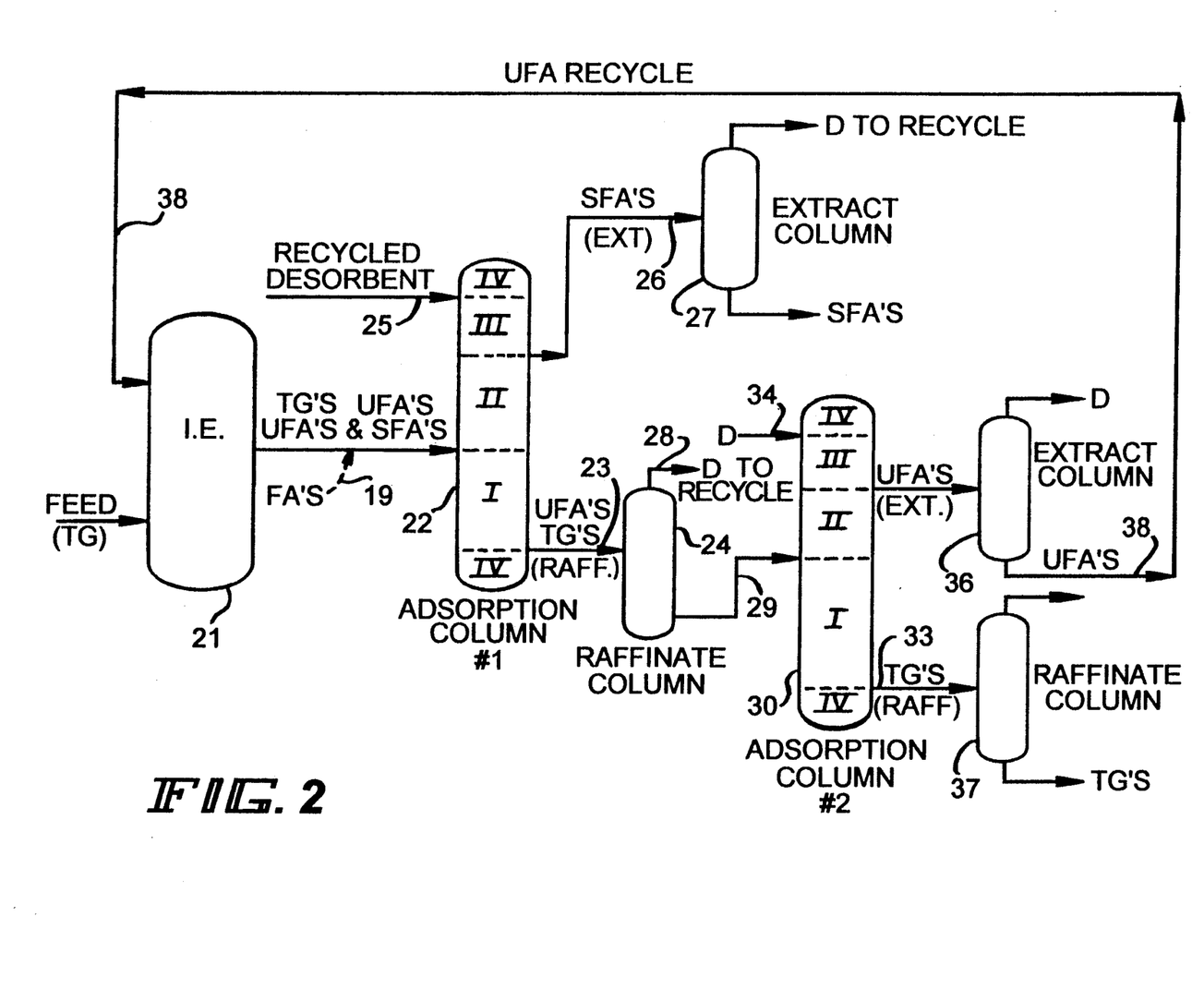
FIG. 2 is an alternative flow scheme for making highly unsaturated triglycerides and recovering unsaturated fatty acids for recycle to the interesterification step of the combined process.

Another embodiment of the invention, a two-stage adsorption separation process, is shown in FIG. 2, in which saturated fatty acids, produced in the interesterification reaction zone 21, are extracted from the interesterification reaction product by adsorption and subsequent desorption in a first adsorption separation column 22 with an adsorbent selective for said saturated fatty acids. The adsorbent preferred for the separation is silicalite. Suitable desorbents for this separation are ketones having from 3 to 8 carbon atoms. The preferred desorbent is 2-heptanone or 3-heptanone and is introduced into column 22 through desorbent inlet line 25. Makeup fatty acids, such as hydrolyzed canola oil, which has a high concentration of unsaturated fatty acids, but also contains substantial amounts of saturated fatty acids, are also introduced into the first stage adsorption separation column 22, via line 20, in order to eliminate saturated fatty acids from the reactant stream 38 to the interesterification reaction.

The raffinate product, comprising unsaturated fatty acids and triglycerides, is removed from column 22 via line 23 and desorbent is recovered via line 28 by fractionating the raffinate fractionation column 24 for recycle to desorbent inlet line 25 of column 22. The bottom stream 29 from column 24, containing the raffinate components from the first adsorption column 22, is directed into the feed inlet of a second adsorption column 30, filled with silicalite adsorbent, which is selective for unsaturated fatty acids and hence, will adsorb the unsaturated fatty acids. Triglycerides are relatively non-adsorbed. The non-adsorbed triglycerides are removed from the column 30 through raffinate output line 33. The adsorbed unsaturated fatty acids are desorbed with a desorbent comprising a ketone or mixture of ketones having from 3 to 8 carbon atoms, although the preferred desorbent for this stage is acetone. The desorbent is introduced in the desorbent input line 34. The unsaturated fatty acids are removed through extract output line 35. Desorbent is recovered from the extract and raffinate streams in the overhead of fractionation columns 36 and 37, respectively, and recycled to desorbent inlet 34.

The unsaturated fatty acids obtained in the above process, are valuable as a reactant in the interesterification reaction and are recycled through reactant stream line 38 to the interesterification column 21. The product triglycerides are separated from the desorbent in raffinate fractionation column 37 and can be utilized in many ways, including those mentioned above.

The saturated fatty acids, obtained as extract in the second stage of the process of FIG. 1 or the first stage of the process of FIG. 2 also have many uses, e.g., in lubricants, in cosmetics after conversion to fatty alcohols and others.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor phase operation. Adsorption conditions will include a temperature range of from about 25° C. to about 200° C. with about 140° C. to about 160° C. being preferred for the separation of saturated fatty acids from unsaturated fatty acids and about 50° C. to about 100° C. being preferred for the separation of triglycerides from free fatty acids and a pressure sufficient to maintain liquid-phase, ranging from about atmospheric to about 500 psig, with from about atmospheric to about 250 psig usually being adequate. Desorption conditions will include the same range of temperatures and pressures as used for adsorption conditions.

A dynamic testing apparatus is employed to test various adsorbents with a particular feed mixture and desorbent material to measure the adsorption characteristics of retention, capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect qualitatively, or determine quantitatively, one or more components in the effluent stream leaving the adsorbent chamber. A pulse test, performed using this apparatus and the following general procedure, is used to determine data, e.g., selectivity, for various adsorbent systems. The adsorbent is placed in a chamber and filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream, or, alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, the rate of desorption of an extract component from the adsorbent and selectivity. The retention volume of an extract or a raffinate component may be characterized by the distance between the center of the peak envelope of the extract or raffinate component and the center of the peak envelope of the tracer component (void volume) or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. Selectivity, $\beta$, is determined by the ratio of the net retention volumes of the more strongly adsorbed component to each of the other components.

The examples shown below are intended to further illustrate the process of this invention without unduly limiting the scope and spirit of the invention.

EXAMPLE Ia

Figure 3:
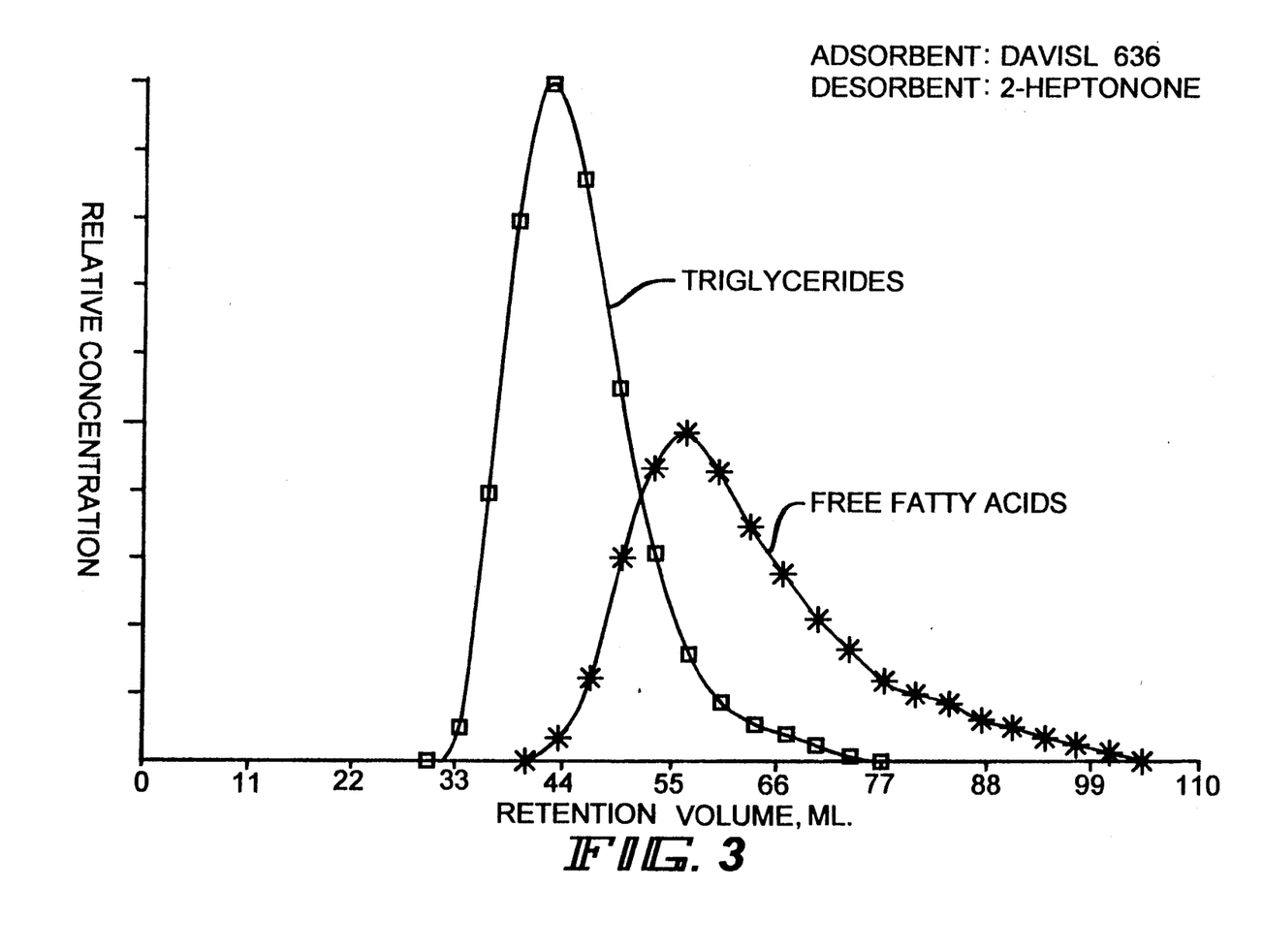
FIGS. 3-8 are chromatographic traces of the separations illustrated in Examples I-IV.

The pulse test described above was performed to demonstrate the first stage of the process of the present invention described in connection with FIG. 1 for separating free fatty acids from triglycerides except that in this test a 35 cc column was used to reduce the volume throughput of desorbent. Flow volumes reported below were doubled to be comparable to the normal 70 cc column. The column was filled with 35 cc of silica gel (Davisil 636 from W. R. Grace Co.) and maintained at a temperature of 37° C. and a pressure sufficient to provide liquid-phase operations. Separate pulses of a mixture of the desorbent and the individual components making up a simulated or typical interesterification reaction product were fed to the pulse test apparatus, in sequence. The simulated interesterification reaction product components were safflower oil and hydrolyzed canola oil. Each pulse consisted of 2 cc of a 0.02% concentration of the component in the desorbent. The hydrolyzed canola oil is a mixture of free fatty acids having the composition in Table 2 above. The safflower oil was a commercially available edible oil containing triglycerides, diglycerides and monoglycerides which had been refined, bleached and deodorized. The desorbent was 2-heptanone. The desorbent material was run continuously at a nominal liquid hourly space velocity (LHSV) of 1 (about 0.6 ml per minute flow rate). At convenient time intervals, the desorbent was stopped and the feed component mixtures were run for a 3.3 minute interval at a rate of 0.6 ml/min. The desorbent stream was then resumed at I LHSV and continued to pass into the adsorbent column until each of the feed components had been eluted from the column as determined by observing the chromatograph generated by the effluent stream leaving the adsorbent column. The chromatograph tracings obtained were overlaid and are shown in FIG. 3. The triglyceride product eluted substantially at the void volume (raffinate) while the adsorbed free fatty acids desorbed last and can be recovered as the extract product. The results are also set forth in the following Table 3 of gross retention volumes (GRV), net retention volumes (NRV) and selectivities ($\beta$) based on a 70 cc column, extrapolated from the data obtained from the 35 cc column.

TABLE 3

| Component | GRV | NRV | Selectivity ($\beta$) |
|---|---|---|---|
| Triglycerides | 44.5 | 4.5 | 4.26 |
| Free Fatty Acids (SFA's + UFA's) | 59.2 | 19.2 | 1.00 (Ref.) |

EXAMPLES Ib AND Ic

Two further pulse tests were run on a 70 cc column to demonstrate the first stage of the process of FIG. 1 using a different adsorbent in combination with methyl ethyl ketone (MEK) as the desorbent. In the first pulse test, the adsorbent was a dealuminated Y having 5 aluminum atoms per unit cell (USY-9 from Toyo Soda). The feed was 5 cc of a solution containing 2 cc of a lipasecatalyzed interesterification reaction product, analyzing 14.2% (wt.) total triglycerides, 26.6% (wt.) linolenic acid, 18.1% (wt.) linoleic acid, 39.3% (wt.) oleic acid, and 0.7% (wt.) of saturated fatty acids, and 3 cc of the desorbent, MEK. The column temperature was 60° C. In the other pulse test, with the same adsorbent-desorbent combination and a column temperature of 100° C., a feed material comprising 5 cc of a mixture of 2 cc of the same interesterification reaction product as Example Ib above, 0.25 g stearic acid and 3 cc MEK was introduced into the column. In both tests, the separation of the triglycerides from all the free fatty acids was clear cut, as indicated by the net retention volumes. The small selectivity differences indicate class separation of fatty acids. The results of the above tests are set forth in the following Table 4.

TABLE 4

| Component | GRV | NRV |
|---|---|---|
| EXAMPLE NO. Ib | | |
| Total Triglycerides | 43.5 | 3.5 |
| Oleic Acid | 50.6 | 10.6 |
| Linolenic Acid | 51.1 | 11.1 |
| Linoleic | 51.5 | 11.5 |
| EXAMPLE NO. Ic | | |
| Total Triglycerides | 47.3 | 7.3 |
| Linolenic Acid | 52.4 | 12.4 |
| Stearic Acid | 52.7 | 12.7 |
| Linoleic Acid | 53.4 | 13.4 |

EXAMPLE II

Figure 4:
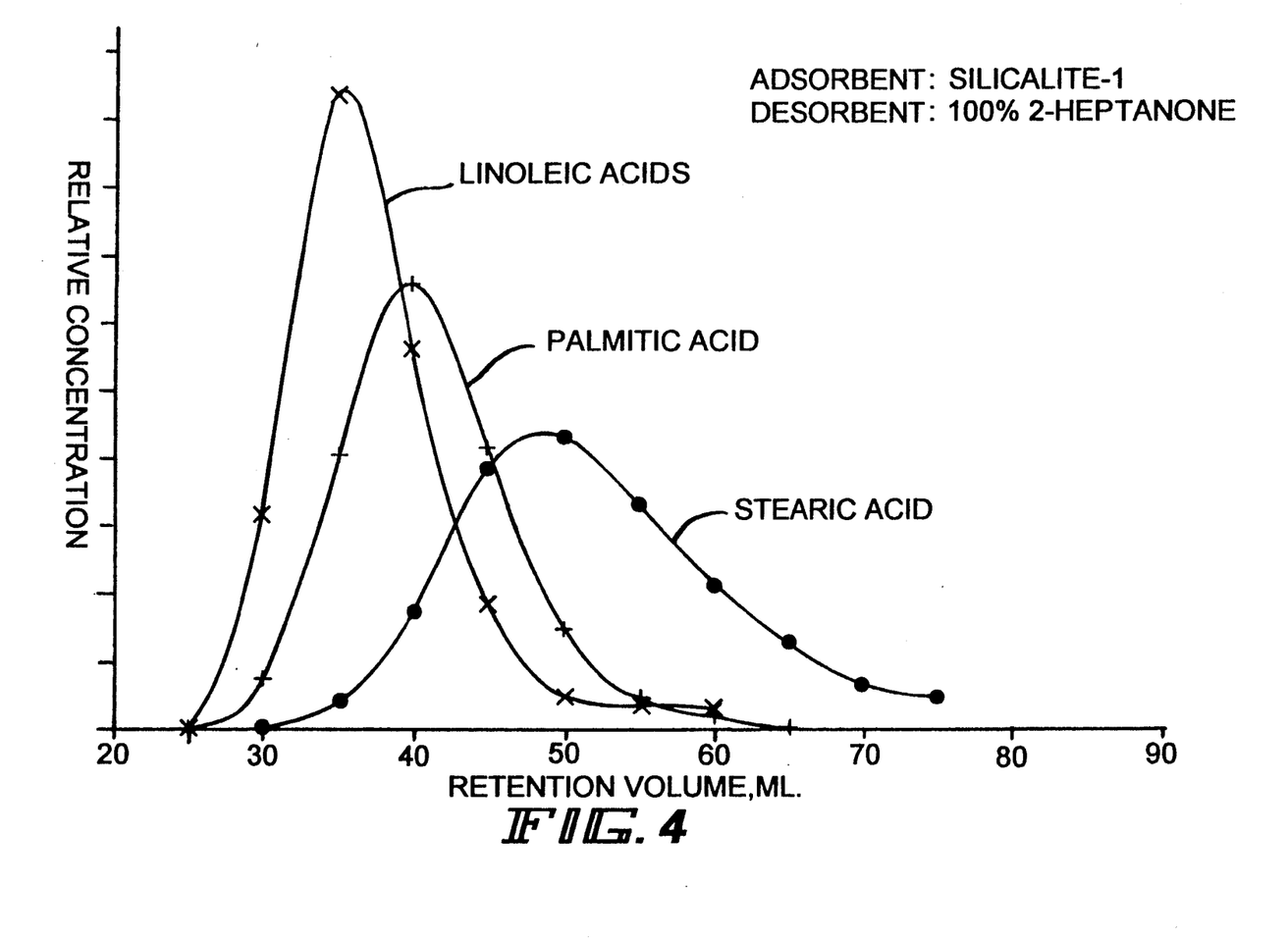

A synthetic mixture of saturated and unsaturated free fatty acids, formulated to simulate the extract product of the first separation stage of Example I, containing equal parts of linoleic acid, palmitic acid, and stearic acid was used as the feed to another pulse test to illustrate the second stage separation of the present invention described in connection with FIG. 1 for separating unsaturated fatty acids from saturated fatty acids. The column was filled with 70 cc of silicalite-1 (UC 115 from Union Carbide Co., now available from UOP) with a silica binder and maintained at a temperature of 180° C. The desorbent was 2-heptanone. Column flow was 1.5 ml/min. Other conditions were the same as Example I. The chromatograph of FIG. 4 was obtained, showing the unsaturated fatty acids removed substantially at the void volume (as raffinate) and the adsorbed components, saturated fatty acids, palmitic and stearic acids, desorbed and recovered (as extract). The results are also set forth in the following Table 5 under the headings gross retention volume (GRV), net retention volume (NRV) and selectivities ($\beta$).

TABLE 5

| Component | GRV | NRV | Selectivity ($\beta$) |
|---|---|---|---|
| Linoleic Acids | 36.2 | 0.0 | $\infty$ |
| Palmitic Acid | 40.2 | 4.0 | 3.54 |
| Stearic Acid | 50.5 | 14.2 | 1.00 (Ref.) |

EXAMPLE III

Figure 5:
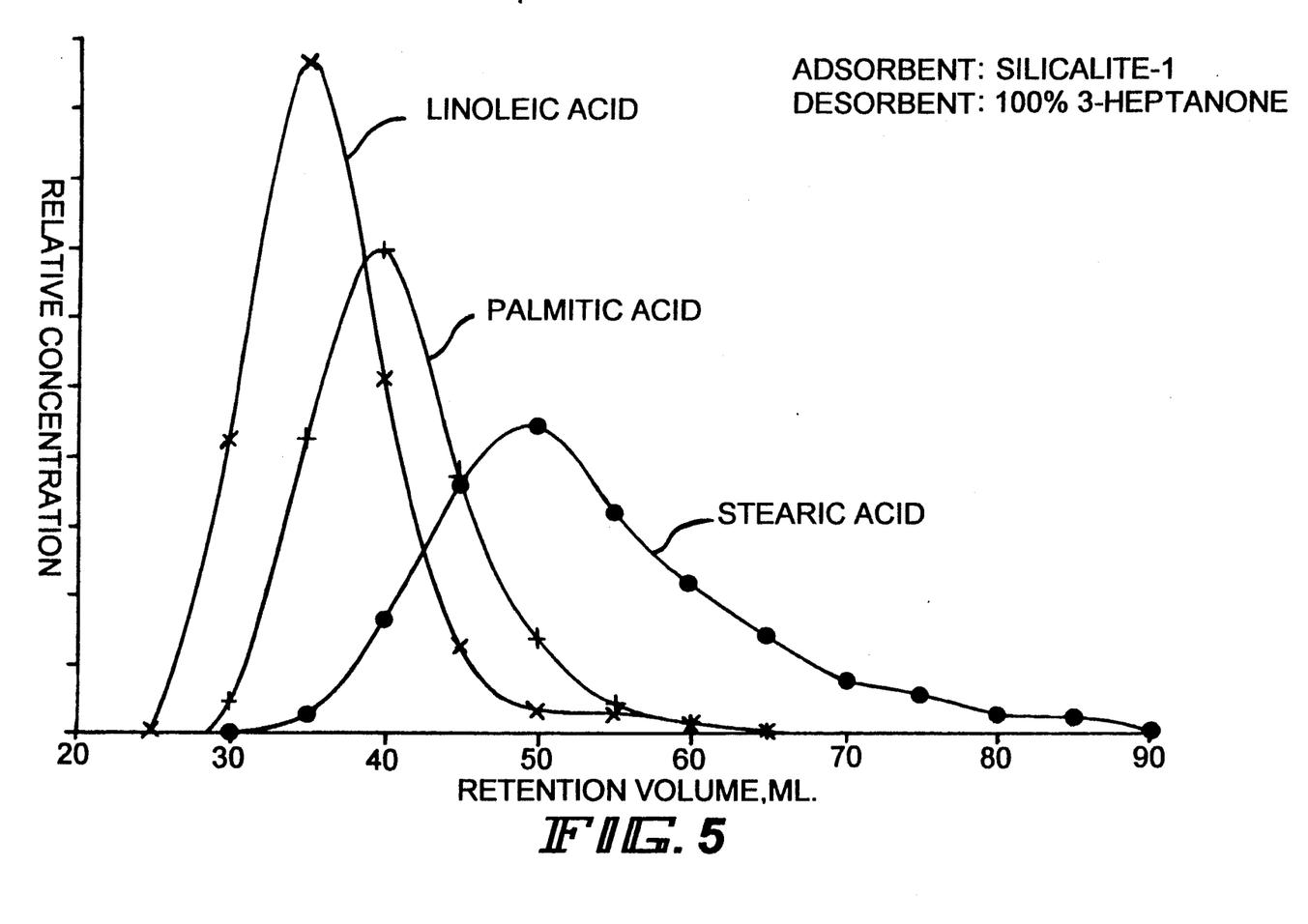

Example II was repeated except that the desorbent was 3-heptanone. Again, the unsaturated fatty acid linoleic acid (C18:2) was separated from the saturated fatty acids, palmitic (C16:0) and stearic acid (C18:0). The results are shown in FIG. 5 and Table 6.

TABLE 6

| Component | GRV | NRV | Selectivity ($\beta$) |
|---|---|---|---|
| Linoleic Acids | 35.5 | 0.0 | $\infty$ |
| Palmitic Acid | 39.7 | 4.2 | 3.57 |
| Stearic Acid | 50.6 | 15.2 | 1.00 (Ref.) |

EXAMPLE IV

Figure 6:
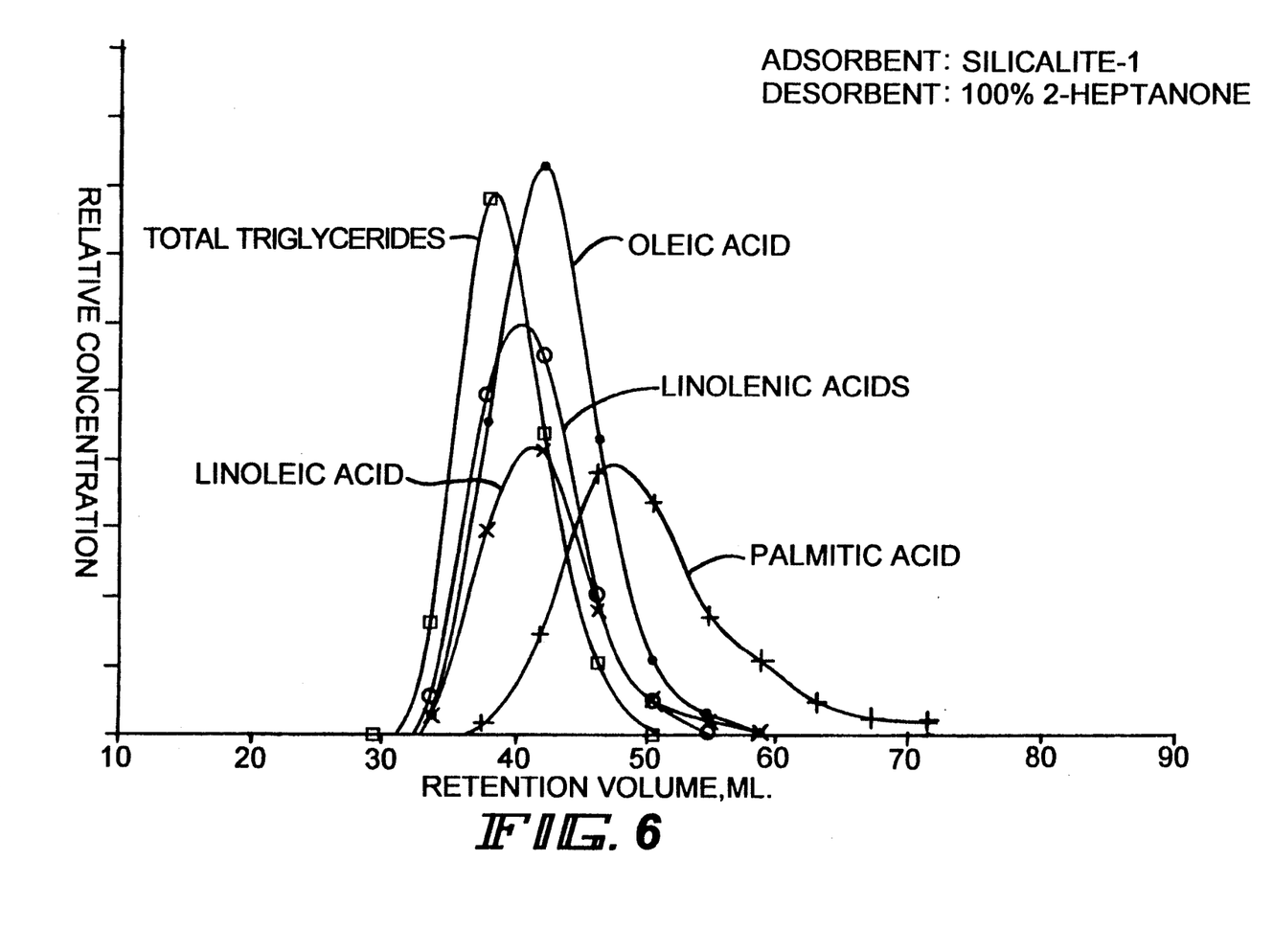

Another series of pulse tests was conducted to demonstrate the two separation stages of the process described in connection with FIG. 2. Two pulse tests were run to demonstrate the first stage separation of saturated fatty acids from unsaturated fatty acids and triglycerides. The conditions and equipment were the same as in Example I, except as noted. The column was filled with silicalite-1 (UC-115). The feed pulse was 5 cc of a mixture containing 1 gram of the oil described in Example Ib plus 0.25 g palmitic acid and 4.5 cc 2-heptanone. The desorbent was 2-heptanone. The column temperature was 150° C. The column flow was 1.25 cc/min. The triglycerides and unsaturated fatty acids were recovered as the raffinate and the most strongly adsorbed saturated fatty acids were desorbed and recovered as the extract. The results are shown in the chromatographs of FIG. 6 and the following Table 7:

TABLE 7

| Component | GRV | NRV | Selectivity ($\beta$) |
|---|---|---|---|
| Total Triglycerides | 38.9 | 0.0 | $\infty$ |
| Linolenic Acid | 40.5 | 1.6 | 5.84 |
| Linoleic Acid | 41.1 | 2.2 | 4.38 |
| Oleic Acid | 41.9 | 3.0 | 3.17 |
| Palmitic Acid | 48.4 | 9.6 | 1.00 (Ref.) |

The second pulse test was run under the same conditions as above, also to demonstrate the first stage separation, except that the feed contained 0.25 g stearic acid, in place of palmitic acid and the column temperature was 175° C. All the unsaturated fatty acids were eluted substantially together immediately after the triglycerides and can be recovered as raffinate while the stearic acid was desorbed and recovered as extract. The results are set forth in FIG. 7 and the following Table 8:

TABLE 8

| Component | GRV | NRV | Selectivity ($\beta$) |
|---|---|---|---|
| Total Triglycerides | 37.3 | 0.1 | $\infty$ |
| Linolenic Acid | 36.8 | 0.0 | $\infty$ |
| Linoleic Acid | 37.2 | 0.6 | 16.7 |
| Oleic Acid | 38.3 | 1.0 | 10.0 |
| Stearic Acid | 46.8 | 10.0 | 1.00 (Ref.) |

Figure 7:
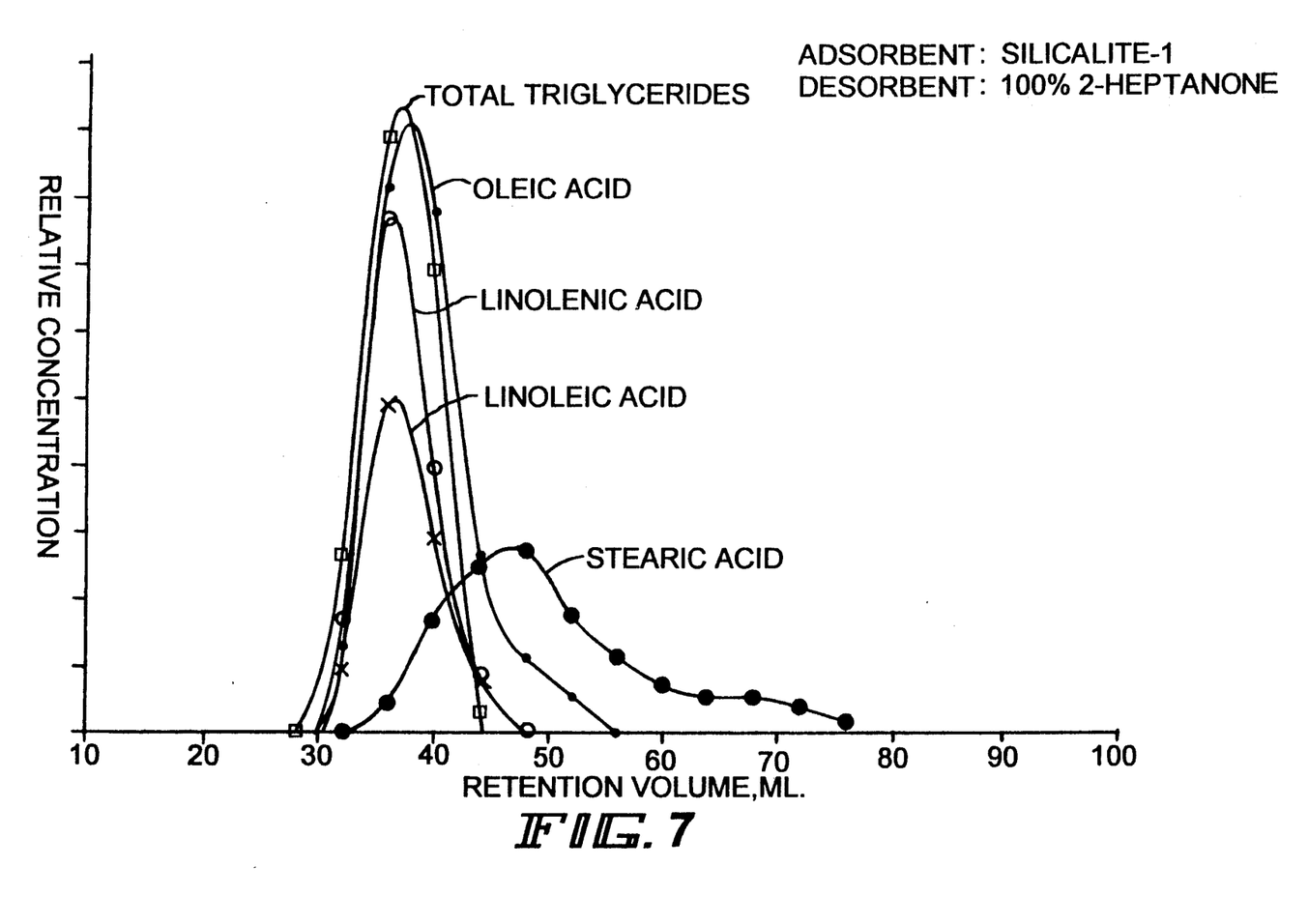

The separation of saturated fatty acids, e.g., palmitic or stearic acids, from unsaturated fatty acids as a group, e.g., oleic, linoleic and linolenic acids, is also possible as demonstrated by the results of these two experiments in FIGS. 6 and 7. As is evident, the elimination of triglycerides from the feed would permit recovery of the group of unsaturated fatty acids in the raffinate and the saturated fatty acids in the extract.

Figure 8:
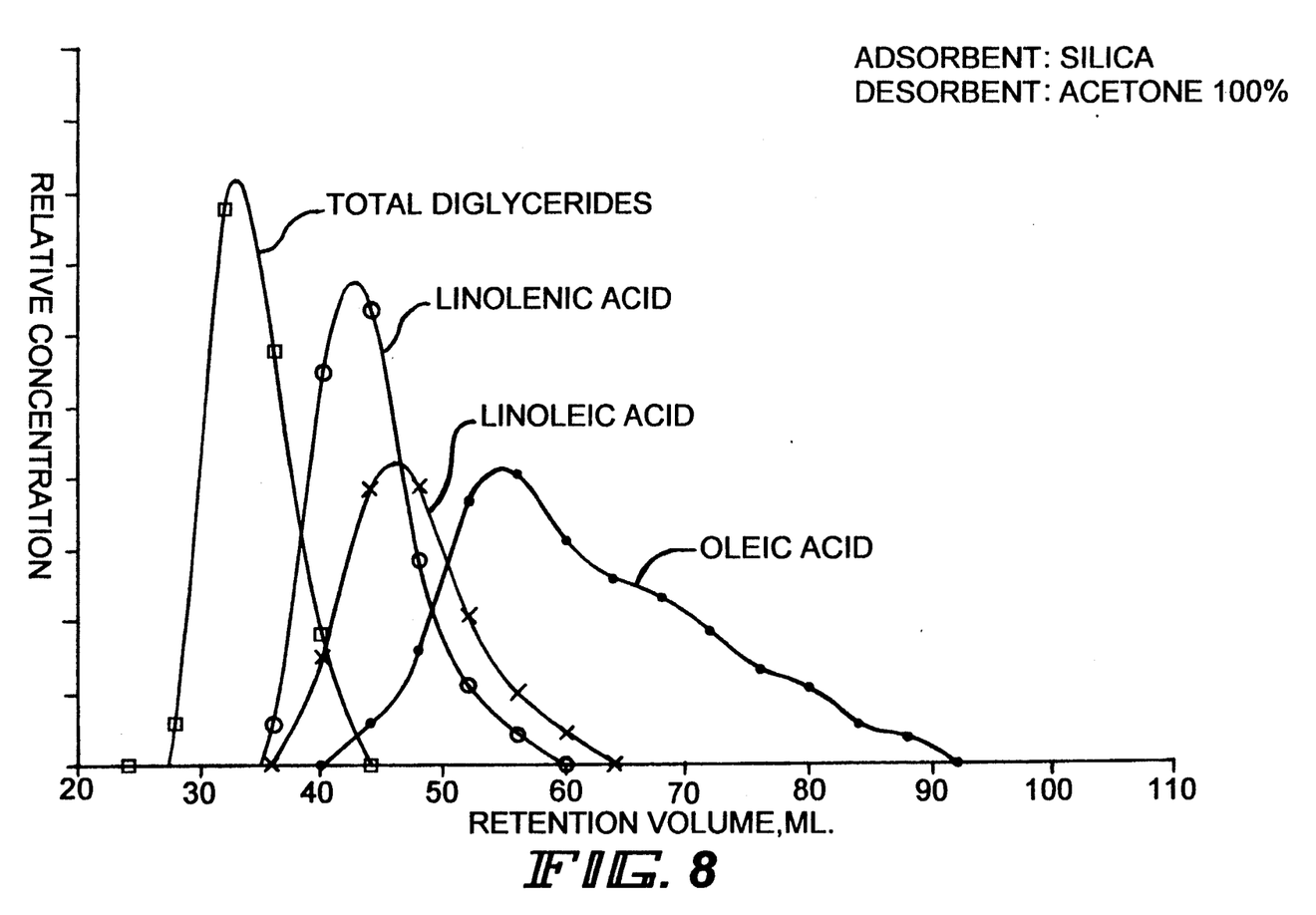

A third pulse test was run to demonstrate the second stage separation of triglycerides from unsaturated fatty acids under the same conditions as Example I, except that the column temperature was 150° C. The feed pulse was 5 cc of a mixture containing 1 cc of a synthetic mixture of triglycerides and unsaturated fatty acids to simulate the raffinate product from the first stage separation and 4 cc of desorbent. The desorbent was acetone. As shown in FIG. 8, the triglycerides are substantially non-adsorbed on the silicalite adsorbent and are eluted near the void volume (as raffinate) and all the unsaturated fatty acids are desorbed and collected as product which can be recycled to the interesterification reaction column. Retention volumes (GRV and NRV) and selectivities are set forth in Table 9.

TABLE 9

| | GRV | NRV | Selectivity ($\beta$) |
|---|---|---|---|
| Total Triglycerides | 33.9 | 0.0 | $\infty$ |
| Linolenic Acid | 42.9 | 9.0 | 2.88 |
| Linoleic Acid | 46.6 | 12.8 | 2.03 |
| Oleic Acid | 59.8 | 25.9 | 1.00 (Ref.) |

EXAMPLE V

This example illustrates my process, when operated in accordance with the embodiment shown in FIG. 1, utilizing in both stages of the separation process, a continuous simulated moving bed countercurrent type of operation comprising a pilot plant scale testing apparatus similar to the manifold arrangement of FIG. 7 described in detail in deRosset et al. U.S. Pat. No. 3,706,812, incorporated herein by reference. Briefly, the apparatus consists essentially of 24 serially connected adsorbent chambers each having about the same volume and a total chamber volume of approximately 1000–1200 cc. The individual adsorbent chambers are serially connected to each other with relatively small diameter connecting piping and to a rotary type valve supplying each of the inlet and outlet streams. By manipulating the rotary valves and maintaining given pressure differentials and flow rates through the various lines passing into and out of the series of chambers, a simulated countercurrent flow is produced. The adsorbent, silica gel (Davisil 636), remains stationary while fluid flows throughout the serially connected chambers in a manner which when viewed from any position within the adsorbent chambers is steady countercurrent flow. The rotary valves are controlled to effect a periodic shifting to allow a new operation to take place in the adsorbent beds located between the active inlet and outlet ports of the rotary valves. Each of the rotary valves is attached to one of the input lines or output lines and directs the respective fluids to and from the individual chambers in sequence. One rotary valve contains a feed input line through which passes the feed mixture, whereby feed can be directed to each of the chambers in a predetermined sequence. A second valve contains an extract stream outlet line through which passes the desorbent material in admixture with free fatty acids, most of the monoglycerides and diglycerides from each of the chambers in sequence. A third and fourth rotary valves contain, respectively, a desorbent material inlet line through which passes desorbent materials to individual chambers and a raffinate stream outlet line through which passes triglycerides and some of the diglycerides in admixture with desorbent material from individual chambers.

The feed mixture to the first adsorption column was a glyceride-free fatty acid-containing mixture, resulting from a lipase-catalyzed interesterification reaction, having the composition given in Table 10. The desorbent was 2-heptanone.

TABLE 10

| Component | Weight Percent |
| --- | --- |
| Triglycerides | 37.4 |
| Free fatty acids (FFA's) | 57.0 |
| Diglycerides | 5.4 |
| Monoglycerides | 0.2 |

The operating parameters of the carousel unit during two periods of the run were as follows:
1. A/F=3.2 and 3.4, where A is the selective pore volume of the adsorbent in ml/hr. and F is the feed rate to the separation stage in ml/hr. The selective pore volume is that volume of the adsorbent which has the ability to selectively adsorb one component of a mixture over another.
2. Process temperature=50° C.
3. Valve cycle time=90 min.

Conditions, however, can vary in practice and to achieve certain performance results. For example, at the process temperature and valve cycle time listed above, zone rates were varied to achieve a range of purity and recovery results.

A number of experiments, each of 6 hours duration, were conducted on the carousel unit. In these experiments, it was observed that the free fatty acids (FFA's) were adsorbed along with the monoglycerides (MG's) and some of the diglycerides (DG's) and so were separated with the extract, while the triglycerides (TG's) and some of the diglycerides were relatively unadsorbed and so were separated with the raffinate. However, the conditions can be set so as to adsorb more diglycerides and, if desired, remove substantially all the diglycerides in the extract. In many food applications, a certain amount of diglycerides may be permitted, e.g., up to about 15%, but preferably about 2–4%, and process conditions may be relaxed making the separation less costly.

The composition of the extract product streams and raffinate product streams for two periods of the first stage separation were as follows:

TABLE 11

| Period | A/F | | FFA's | MG's | DG's | TG's |
| --- | --- | --- | --- | --- | --- | --- |
| 1 | 3.2 | Raff. | 0.6 | 0.2 | 0.2 | 99.0 |
| | | Extract | 86.5 | 0.7 | 11.3 | 1.5 |
| 2 | 3.4 | Raff. | 1.5 | 0.1 | 2.8 | 95.6 |
| | | Extract | 90.6 | 0.6 | 8.8 | 0 |

Figure 9:
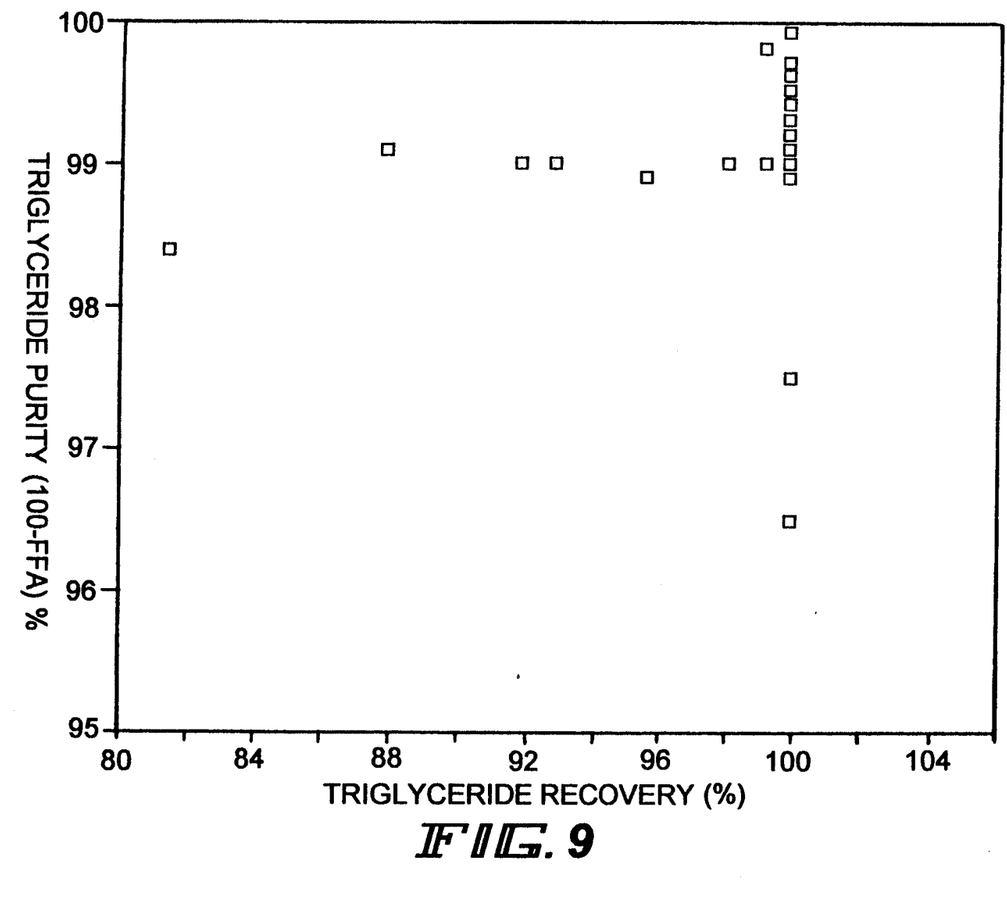
FIG. 9 is a plot of purity vs. recovery of triglycerides from the first stage separation of Example V.

The extract and raffinate streams from all the experiments described above were analyzed for their monoglyceride, fatty acid and di- and triglyceride content. The results of these experiments were plotted and are shown in FIG. 9 as a curve of triglyceride raffinate purity versus triglyceride recovery. The separation performance ranged from triglyceride purity of 95.6–99+% at 99+% recovery. The triglyceride raffinate product can be further freed of any remaining fatty acids where the content is below about 1% by cooling the extract to 0° C., whereupon the triglycerides will precipitate and can be filtered from the remaining mixture of desorbent and fatty acids.

To separate the unsaturated fatty acids from the saturated fatty acids, the extract from the first stage separation is introudced to the second separation column together with makeup fatty acids, preferably a mixture of unsaturated fatty acids and saturated fatty acids high in unsaturated content. Since the extract stream will be small in comparison to the makeup fatty acids, the combined feed will be close in proportions of components of the makeup fatty acids. In the illustration of the second stage separation which follows, therefore, a mixture of unsaturated fatty acids and saturated fatty acids derived by hydrolysis of canola oil (see Table 2) was fed to an adsorption column filled with silicalite-1 (UC 115-1 from UOP).

The adsorbent used for the saturated fatty acid/unsaturated fatty acid separation was silicalite. The desorbent was 2-heptanone. The operating parameters of the pilot plant were as follows:
1. A/F=3, where A is the selective pore volume of the adsorbent in ml/hr. and F is the feed rate in ml/hr.
2. Process temperature=150 C.
3. Valve cycle time=90 minutes.

A series of experiments, each of six hours duration, was conducted in a pilot plant having a total capacity of about 1056 ml. It was observed that the saturated fatty acids, especially those of relatively high content in the feed like palmitic and stearic acids, were extracted, while the unsaturated fatty acids were relatively unadsorbed and hence separated to form the raffinate.

Figure 10:
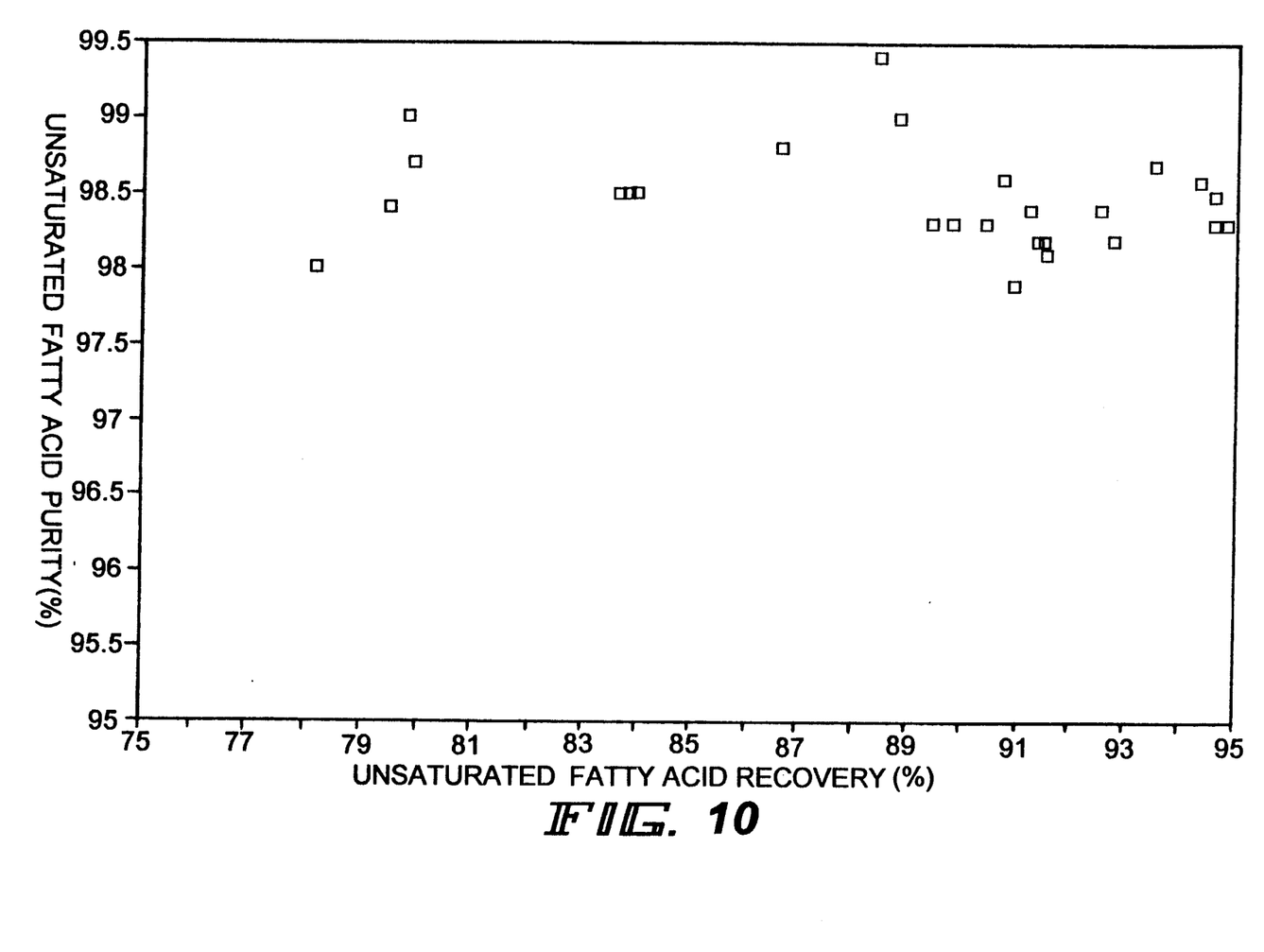
FIG. 10 is a plot of purity vs. recovery of unsaturated fatty acids from the second stage separation of Example V.

The extract and raffinate streams were again analyzed for their component concentrations. Since the ultimate objective in this stage is to produce pure unsaturated fatty acids to recycle to the interesterification reaction where more unsaturated triglycerides are produced, the raffinate is the desired product. The results were plotted, as a graph of unsaturated fatty acid raffinate purity vs. unsaturated fatty acid raffinate recovery in FIG. 10. Thus, 98% or greater unsaturated fatty acid purity and recovery of up to 94% or greater of the unsaturated fatty acids was achieved.

The saturated fatty acid extract also has many uses; for example, it can be used to make lubricants, or can be converted to the corresponding fatty alcohols for use in cosmetics and other applications.

The compositions of a typical extract product stream and raffinate stream were as follows:

TABLE 12

| Fatty Acid | Raffinate | Extract |
| --- | --- | --- |
| C14:0 + C13:0 | 0.0 | 0.4 |
| C14:1 | 0.3 | 0.4 |
| C16:0 | 0.2 | 20.3 |
| C16:1 | 0.2 | 0 |
| C18:0 | 0.4 | 11.6 |
| C18:1 | 62.6 | 35.6 |
| C18:1 (trans) | 2.6 | 4.4 |
| C18:2 | 20.1 | 4.2 |
| C18:2 | 0.4 | 0.2 |
| C18:3 | 1.2 | 0.4 |
| C18:3 | 7.2 | 1.5 |
| C18:3 | 1.3 | 0.5 |
| C20:0 | 0.1 | 3.2 |
| C20:1 | 0.4 | 6.7 |
| C22:0 | 0.1 | 1.3 |
| C22:1 | 0.1 | 1.6 |
| UNKNOWNS | 2.8 | 7.7 |

Raffinate product obtained from a number of 6 hour experiments of the second stage separation just described were combined and reacted with a triglyceride oil in an interesterification reaction zone and the highly unsaturated triglyceride product, analyzing 41.3% (wt) triglycerides, 8.4% (wt) diglycerides, 0.5% (wt) monoglycerides and 49.8% (wt) free fatty acids was directed to the first separation column, using the same adsorbent and desorbent.

The operation parameters during this run were:
1. A/F=3
2. Process Temperature=50° C.
3. Valve Cycle Time=90 min.

The composition of the extract and raffinate product streams were as follows:

TABLE 13

|  | FFA's | MG's | DG's | TG's |
| --- | --- | --- | --- | --- |
| Raffinate | 0.9 | 0.1 | 1.3 | 97.7 |
| Extract | 86.2 | 0.7 | 10.3 | 2.8 |

For this period 96% of the triglycerides were recovered at 97.7% purity.

What is claimed is:

1. A two-stage chromatographic separation process for recovering polyunsaturated triglycerides from an interesterification reaction comprising treating a mixture of a triglyceride oil or fat and an unsaturated fatty acid or mixture of unsaturated fatty acids with an interesterification catalyst to increase the degree of unsaturation of said triglyceride oil or fat, contacting said treated triglyceride oil or fat in a first stage with an adsorbent more selective for saturated fatty acids than for triglycerides, removing a first raffinate product stream comprising polyunsaturated triglycerides produced in said interesterification reaction from said adsorbent, desorbing the saturated fatty acids produced in the interesterification reaction with a desorbent, at desorption conditions, to produce a first extract product stream, contacting the product stream from said first stage containing unreacted unsaturated fatty acids with a second adsorbent, in a second stage, capable of separating said unsaturated fatty acids from said first stage product stream, recovering said unsaturated fatty acids from said second adsorbent and recycling said unsaturated fatty acids to said interesterification reaction and recovering a raffinate product comprising polyunsaturated triglycerides.

2. The process according to claim 1 wherein said first adsorbent is selected from the group consisting of dealuminated Y zeolites, silicalite and silica gel.

3. The process according to claim 1 wherein said first desorbent is selected from the group consisting of ketones having from 3 to 8 carbon atoms, ethers and esters.

4. The process according to claim 1 wherein said first desorbent is a ketone having from 3 to 8 carbon atoms.

5. The process according to claim 4 wherein said desorbent is heptanone.

6. The process according to claim 5 wherein said desorbent is 2-heptanone.

7. The process according to claim 5 wherein said desorbent is 3-heptanone.

8. The process according to claim 1 wherein said second adsorbent is silicate.

9. The process according to claim 1 wherein the first stage product stream is an extract stream containing unsaturated fatty acids and saturated fatty acids and said raffinate product is recovered from said first stage.

10. The process according to claim 1 wherein the first stage product stream is a raffinate stream containing unsaturated fatty acids and polyunsaturated triglycerides and said raffinate product is recovered from said second stage.

11. The process according to claim 9 wherein said second adsorbent is desorbed with a second desorbent comprising a ketone having from 3 to 8 carbon atoms, at desorption conditions.

12. The process according to claim 11 wherein said second desorbent is 2-heptanone.

13. The process according to claim 10 wherein said second adsorbent is desorbed with a second desorbent, comprising a ketone having from 3 to 8 carbon atoms, at desorption conditions.

14. The process according to claim 13 wherein said second desorbent is acetone.

15. A two-stage chromatographic separation process for recovering polyunsaturated triglycerides from an interesterification reaction comprising treating a mixture of a triglyceride oil or fat and an unsaturated fatty acid with an interesterification catalyst to increase the degree of unsaturation of said triglyceride oil or fat, contacting said treated triglyceride with an adsorbent selective for saturated fatty acids, removing a raffinate comprising unreacted unsaturated fatty acids and the polyunsaturated triglycerides produced in said interesterification reaction from said adsorbent, desorbing the saturated fatty acids produced in said interesterification reaction with a desorbent comprising a ketone having from 3 to 8 carbon atoms, at desorption conditions, to produce an extract product stream, contacting said raffinate with a second adsorbent more selective for said unsaturated fatty acids, removing a second raffinate material comprising said polyunsaturated triglycerides, desorbing said unsaturated fatty acids with a desorbent comprising a ketone having from 3 to 8 carbon atoms, at desorption conditions and recycling said unsaturated fatty acids to said interesterification reaction.

16. A two-stage chromatographic separation process for recovering polyunsaturated triglycerides from an interesterification reaction comprising treating a mixture of a triglyceride oil or fat and an unsaturated fatty acid with an interesterification catalyst to increase the degree of unsaturation of said triglyceride oil or fat, contacting said treated triglyceride oil or fat in a first stage with an adsorbent selective for fatty acids, removing a raffinate material comprising polyunsaturated triglycerides produced in said interesterification reaction from said adsorbent, desorbing the saturated fatty acids produced in said interesterification reaction and unreacted unsaturated fatty acids with a desorbent comprising a ketone having from 3 to 8 carbon atoms, at desorption conditions, to produce a first extract product, contacting said first extract product from said first stage with a second adsorbent more selective for saturated fatty acids than unsaturated fatty acids, removing a second raffinate material comprising unsaturated fatty acids, recycling said unsaturated fatty acids to said interesterification reaction and desorbing saturated fatty acids with a desorbent comprising a ketone having from 3 to 8 carbon atoms, at desorption conditions.

* * * * *